United States Patent [19]

Belykh et al.

[11] 4,263,185

[45] Apr. 21, 1981

[54] BIODESTRUCTIVE MATERIAL FOR BONE FIXATION ELEMENTS

[76] Inventors: Sergei I. Belykh, 2 Krestovsky pereulok, 4, kv. 66, Moscow; Anatoly B. Davydov, ulitsa Krasny Kazanets, 19, korpus 1, kv. 283, Moscow; Gennady L. Khromov, 2 Frunzenskaya, 10, kv. 100, Moscow; Anatoly D. Moschensky, poselok Malakhovka, Bykovskoe shosse, 41, kv. 66, Moskovskaya oblast; Ilya A. Movshovich, Scherbakovskaya ulitsa, 8-12, kv. 33, Moscow; Gennady I. Roitberg, Teply Stan, korpus 27, kv. 375, Moscow; Gennady L. Voskresensky, ulitsa Chkalova, 25, kv. 32, Moscow; Gely G. Pershin, Krivorozhskaya ulitsa, 9, kv. 62, Moscow; Valery A. Moskvitin, ulitsa Mostovaya, 4, kv. 89, Belgorod-Dnestrovsky Odesskoi oblasti, all of U.S.S.R.

[21] Appl. No.: 80,296

[22] Filed: Oct. 1, 1979

[51] Int. Cl.³ .................. C08L 77/06; C08L 39/06; C08L 33/26; C08L 33/10; C08L 1/04
[52] U.S. Cl. .................. 260/17.4 R; 260/8; 128/92 G; 128/156; 128/92 C; 128/92 CA; 525/57; 525/178
[58] Field of Search .............. 260/8, 17.4, 42.14, 260/29.6 HN; 525/57, 178; 128/92 G, 92 C, 92 CA, DIG. 8, 156; 526/264

[56] References Cited

U.S. PATENT DOCUMENTS

| | | | |
|---|---|---|---|
| 3,142,664 | 7/1964 | Bauer | 526/264 |
| 3,806,350 | 4/1974 | Kuhn et al. | 260/6 |
| 3,888,975 | 6/1975 | Ramwell | 424/22 |
| 3,943,045 | 3/1976 | Cordrey et al. | 128/156 |
| 4,036,814 | 7/1977 | Howes et al. | 526/264 |
| 4,112,215 | 9/1978 | Boessler et al. | 526/264 |

FOREIGN PATENT DOCUMENTS 888046  1/1962  United Kingdom ............ 525/57

*Primary Examiner*—V. P. Hoke
*Attorney, Agent, or Firm*—Burgess, Ryan and Wayne

[57] ABSTRACT

This invention relates to medical technique and more particularly it relates to biodestructive materials used to manufacture elements for fixation of bone fragments.

Said material contains a matrix of non-toxic polymer resolvable in the body consisting of hydrophilic and hydrophobic repeat units, and a reinforcing component of non-toxic fibres or threads resolvable in the body. The matrix polymer is preferably a copolymer of methyl methacrylate and N-vinyl pyrrolidone, and the reinforcing component is preferably fibre or threads of polyamide and oxycellulose.

Said material can be used in medicine for fixation of bone fragments in fractures or injuries of bones.

6 Claims, No Drawings

BIODESTRUCTIVE MATERIAL FOR BONE FIXATION ELEMENTS

This invention relates to medical technique, and more particularly it relates to biodestructive materials used for fixation of bone tissues.

FIELD OF THE INVENTION

Biodestructive material can be used in medical technique for the manufacture of connecting elements for rendering medical aid in injuries. Such elements are, for example, various pins, staples, rods, plates, etc., intended for fixation of bones in fractures.

BACKGROUND OF THE INVENTION

Known in the prior art are various connecting elements manufactured from metal alloys. But they have certain disadvantages, which are in the first instance associated with the removal of the fixation elements from the regenerated bone by surgical methods. Moreover, metal alloys often produce marked reactions in bone tissues, and even gas and toxic products can be produced by alloys containing magnesium.

Attempts were made to use polymers, e.g. polymethyl methacrylate, for the manufacture of bone fixation elements (Blumin, I. I. Kheifitz, A. V., "Vestnik Khirurghii i Anesteziologhii," 1955, 11, 80–83). But polymethyl methacrylate does not have the required strength and is not resolved in the body, which again involves repeated operations for extraction of the fixtures.

Known in the prior art are also methods for the manufacture of bone fixation elements from the protein fractions of human blood (Golovin, G. V., "Voprosy Vosstanovitelnoi Khirurghii, Travmatologhii i Ortopedii", Sverdlovsk, 1957, 6, 211–217). But the physico-mechanical properties of such materials do not meet the requirements, while the time of its resolution in the body is shorter than the time required for the regeneration of the bone tissue.

Attempts were made to use materials consisting of a reinforcing component in the form of fibres or fibric, for example, glass fibre, carbon fibre, glass fabrics, and a polymer binding component, for example, unsaturated polyester, epoxy, polyamide, etc., but despite the high strength, bone connective fixtures manufactured out of these materials proved ineffective because they are either toxic or do not resolve in the body.

OBJECT OF THE INVENTION

The object of the invention is to provide a biodestructive material for the manufacture of bone fixation elements which would be able to resolve in the body at the wanted terms, would be harmless, and would possess the high physico-mechanical properties ensuring reliable fixation of bone fragments.

SUMMARY OF THE INVENTION

According to the invention, proposed is a biodestructive material for the manufacture of bone fixation elements comprising a matrix of a non-toxic resolvable polymer consisting of hydrophilic and hydrophobic repeat units, and a reinforcing component made out of non-toxic resolvable fibres or threads.

The hydrophillic units, which enter into the matrix polymer are, for example, n-vinyl pyrrolidone, acrylamide, vinyl caprolactam, monomethacrylic ester of ethylene glycol, methacrylamide, acrylic acid, and also any other compound which forms water-soluble non-toxic polymers or polymers unlimitedly swellable in water.

The hydrophobic units which enter into the matrix polymer are, for example, methyl methacrylate, butyl methacrylate, vinyl acetate, alpha-ethoxycyanacrylate, ethyl acrylate, and also other compounds which form non-toxic water-insoluble polymers.

The fibres used as reinforcement for the bone fixation elements are, for example, synthetic non-toxic fibres or threads of polyamide, oxycellulose, polyvinyl alcohol, or their mixtures, and also natural non-toxic resolvable fibres and threads, such as catgut, collagen, dextran fibres and threads, and the like.

DETAILED DESCRIPTION OF THE INVENTION

As has been stated above, proposed is a novel biodestructive material used for fixation of bone fragments, which, according to the invention, comprises a matrix of a non-toxic polymer formed from hydrophilic and hydrophobic units and a reinforcing component of non-toxic threads or fibres resolvable in the body.

Said polymer is prepared by the known method, i.e. by polymerization or copolymerization of the starting hydrophilic and hydrophobic monomers in a medium of inert solvents, for example, in benzene, toluene, in the presence of initiators of radical polymerisation, for example, dinitrileazo-bis-isobutyric acid, or 4,4-azo-bis-(4-cyanpentonic)acid. It is recommended that the finished polymer contained from 20 to 40 percent by weight of hydrophilic units, which ensures better results.

If the polymer contains less than 20 percent of hydrophilic units, the biodestruction of the polymer in the patient body will be more protracted. If the matrix polymer contains more than 40 percent of the hydrophilic units, the material swells in excess and does not ensure the required strength of the material during the period of bone fragment consolidation.

The process for the manufacture of the biodestructive material consists in that the starting polymer is dissolved in an inert organic solvent, for example, in acetone, toluene, or ethyl acetate, and the obtained solution is used to impregnate threads or fibres of the reinforcing component. The material is then dried to remove the solvent. The obtained material contains the matrix in the quantity from 20 to 50 percent and the reinforcing component from 50 to 80 percent by weight. Said weight proportions of the matrix and the reinforcing component ensure the required physico-mechanical properties of the material intended for the fixation of fractured bones.

The proposed biodestructive material offers the following advantages:

1. It rules out the necessity of an additional operation for the extraction of the connecting element.

2. Makes it possible to adjust the size of the connecting element straight during the operation by using mechanical tools so that it might fit properly each particular fragment of bone without limiting mobility of the adjacent joints during the period of the bone fragment consolidation.

Various connecting elements, such as pins, rods, staples, can be manufactured out of the proposed biodestructive material; it is placed into compression moulds and pressed at a temperature of 200° C. and specific pressure to 300 kg/sq.cm. The mould is then cooled and the finished article extracted.

It is recommended to use a biodestructive material in which the matrix is a copolymer of methyl methacrylate and N-vinyl pyrrolidone, and the reinforcing element is polyamide fibre. The starting components of this material are readily available commercial products, and the physico-mechanical properties of the resulting material adequately meet the requirements.

For a better understanding of the invention, the following examples of its practical embodiment are given by way illustration.

EXAMPLE 1

28.8 g of polyamide fibre are impregnated with acetone solution containing 11.2 g of copolymer of methyl methacrylate and N-vinyl pyrrolidone. The content of N-vinyl pyrrolidone in the copolymer is 31.2 percent by weight. The fibre is then dried to remove the solvent and the obtained material is placed in a compression mould where it is pressed at a temperature of 160° C. and a pressure of 280 kg/sq.cm. The mould is then cooled to a temperature of 40° C., the pressure is released, and the article removed from the mould.

The article prepared in this example is a rod, 12 mm in diameter and 410 mm long. It has the following characteristics:

| | |
|---|---|
| flexing strength | 2700 kg/sq.cm |
| elasticity modulus in bend | 45,200 kg/sq.cm |
| resolution time in a living body | about two years |
| period of reliable fixation of bone fragments | 8–9 months |

EXAMPLE 2

The biodestructive material and the article out of it are prepared by the procedure described in Example 1, except that 8 g of the copolymer of methyl methacrylate and N-vinyl pyrrolidone and 32 g of polyamide fibre are used. The finished article is a rod having the same dimensions as in Example 1. Its characteristics are as follows:

| | |
|---|---|
| flexing strength | 2400 kg/sq.cm |
| elasticity modulus in bend | 32,600 kg/sq.cm |
| resolution time | about two years |
| period of reliable fixation of bone fragments | 8–9 months |

EXAMPLE 3

The biodestructive material and the connective element out of it are prepared by the procedure described in Example 1 except that 20 g of the copolymer of methyl methacrylate and N-vinyl pyrrolidone and 20 g of polyamide fibre are used. The article manufactured of this material is a rod having the same dimensions as specified in Example 1. The rod has the following characteristics:

| | |
|---|---|
| flexing strength | 2610 kg/sq.cm |
| elasticity modulus in bend | 39,400 kg/sq.cm |
| resolution time | about two years |
| period of reliable fixation of bone fragments | 8–9 months |

EXAMPLE 4

A biodestructive material, prepared from 30.1 g of the copolymer of methyl methacrylate and N-vinyl pyrrolidone (N-vinyl pyrrolidone content is 39.6 percent by weight) and 66.9 g of carboxyethyl cellulose fibre (PD 330), is used for the manufacture of a rod, 13 mm in diameter and 415 mm long. The procedure is the same as described in Example 1. The rod has the following characteristics:

| | |
|---|---|
| flexing strength | 1890 kg/sq.cm |
| elasticity modulus in bend | 25,000 kg/sq. cm |
| resolution time | 1.7 year |
| period of reliable fixation of bone fragments | 4.5–6 months |

EXAMPLE 5

The biodestructive material and the article out of it are prepared by a procedure described in Example 1, except that 28.2 g of the copolymer of methyl methacrylate and N-vinyl pyrrolidone (N-vinyl pyrrolidone content of the copolymer being 33.6 percent by weight) and 64.7 g of polyamide fibre and 4.1 g of carboxymethyl cellulose fibre are used. The rod manufactured out of this material has the dimensions specified in Example 4 and is characterized by the following properties:

| | |
|---|---|
| flexing strength | 2840 kg/sq.cm |
| elasticity modulus in bend | 25,000 kg/sq.cm |
| resolution time | 21 months |
| period of reliable fixation of bone fragments | 5–7 months |

EXAMPLE 6

The biodestructive material and the connective element out of it are manufactured by the procedure described in Example 1, except that 20.1 g of the copolymer of methyl methacrylate and N-vinyl pyrrolidone (N-vinyl pyrrolidone content of the copolymer being 35.2 percent by weight) and 12.7 g of catgut fibres, and 38.2 g of polyamide fibres are used to prepare the material. The fixation rod manufactured from this material has the dimensions specified in Example 4 and is characterized by the following properties:

| | |
|---|---|
| flexing strength | 2160 kg/sq.cm |
| elasticity modulus in bend | 9800 kg/sq.cm |
| resolution time | 1.4 year |
| period of reliable fixation of bone fragments | 3–5 months |

EXAMPLE 7

The biodestructive material and the connecting elements out of it are prepared by the procedure described in Example 1, except that 20.1 g of a copolymer of butylmethacrylate and N-vinyl pyrrolidone, and 69.2 g of polyamide fibre are used to manufacture the material. The rod prepared from this material has the following characteristics:

| | |
|---|---|
| flexing strength | 1920 kg/sq.cm |

| | |
|---|---|
| elasticity modulus in bend | 9200 kg/sq.cm |
| resolution time | 2.7 year |
| period of reliable fixation of bone fragments | 9 months |

EXAMPLE 8

The biodestructive material and the connecting element out of it are manufactured by the procedure described in Example 1, except that 32 g of a copolymer of acrylamide and ethyl acrylate (the acrylamide content of the copolymer being 22 percent by weight), and 69 g of carboxyethyl cellulose fibres are used to prepare the material. The article manufactured from this material is a fixation rod having the following characteristics:

| | |
|---|---|
| flexing strength | 1790 kg/sq.cm |
| elasticity modulus in bend | 8700 kg/sq.cm |
| resolution time | 1.3 year |
| period of reliable fixation of bone fragments | 3-5 months |

What is claimed is:

1. A biodestructive material for bone fixation elements comprising from 20 to 50 percent by weight of a matrix of a non-toxic body resolvable copolymer consisting essentially of 20 to 40 percent by weight of hydrophilic monomer units and 80 to 60 percent by weight of hydrophobic monomer units, and 80 to 50 percent by weight of a reinforcing component made of a non-toxic and body resolvable threads or fibers wherein said hydrophilic monomer units are selected from the group consisting of N-vinyl pyrrolidone, hydrophobic acrylamides, vinyl caprolatam, the mono methacrylic acid ester of ethylene glycol and acrylic acid, the hydrophobic monomer units are selected from the groups consisting of hydrophobic acrylates and vinyl acetate, and the resolvable threads or fibers are selected from the group consisting of polyamide, oxy cellulose, polyvinyl alcohol and naturally-occurring non toxic resolvable fibers.

2. A material of claim 1, wherein the hydrophilic monomer units in the matrix polymer are N-vinyl pyrrolidone or acrylamide units.

3. A material of claim 1, wherein the hydrophobic monomer units of the matrix polymer are alkyl acrylate monomer units.

4. A material of claim 3 wherein the alkyl acrylate is methyl methacrylate.

5. A material of claim 1 or 2 or 3 or 4, wherein the reinforcing component comprises fibers or threads selected from the group consisting of polyamide, oxycellulose, polyvinyl alcohol and mixtures thereof.

6. A material of claim 1 wherein the matrix is a copolymer of methyl methacrylate and N-vinyl pyrrolidone, in which N-vinyl pyrrolidone monomer units comprises 25-28 percent by weight and the reinforcing component comprises polyamide fibers.

* * * * *